United States Patent [19]

Christensson

[11] Patent Number: 5,295,872
[45] Date of Patent: Mar. 22, 1994

[54] BIOMEDICAL ELECTRICAL CLASP

[76] Inventor: Eddy K. G. Christensson, 4016 Inglewood Ave. So., Edina, Minn. 55416

[21] Appl. No.: 908,397
[22] Filed: Jul. 6, 1992
[51] Int. Cl.⁵ .............................................. H01R 4/48
[52] U.S. Cl. .................................. 439/822; 439/909
[58] Field of Search ............. 439/217, 218, 219, 729, 439/819, 822, 829, 909; 128/639, 641

[56] References Cited

U.S. PATENT DOCUMENTS

| | | | |
|---|---|---|---|
| 2,465,722 | 5/1946 | Hamilton | 173/273 |
| 3,090,029 | 5/1963 | Stroebel | 439/822 |
| 3,456,181 | 7/1969 | Godshalk | 320/25 |
| 3,842,394 | 10/1974 | Bolduc | 439/261 |
| 3,868,165 | 2/1975 | Gonser | 339/97 R |
| 3,914,007 | 10/1975 | Seidler | 339/255 P |
| 4,040,697 | 8/1977 | Ramsay et al. | 439/822 |
| 4,151,462 | 4/1979 | Teyler | 439/829 |
| 4,449,772 | 5/1984 | Johnson, III | 339/29 B |
| 4,453,791 | 6/1984 | Ledbetter | 339/29 B |
| 4,640,563 | 2/1987 | LeBlanc | 339/32 M |
| 4,702,256 | 10/1987 | Robinson et al. | 439/909 |
| 4,797,125 | 1/1989 | Malana | 439/909 |

OTHER PUBLICATIONS

Commercial Product: EKG Clip by Hirshman of America, Riverdale, N.J.
Commercial Product: "Astro-Trace" Clip by LeBlanc Corporation of Augusta, Ga.
Commercial Product: Trono MEd EKG Clip by Trono MEd, Inc. of Irvine, Calif.

Primary Examiner—Larry I. Schwartz
Assistant Examiner—Hien D. Vu
Attorney, Agent, or Firm—James V. Harmon

[57] ABSTRACT

This invention provides a spring-operated biomedical electrical clasp which includes a clasp base means and a clasp lever, each having a handle end and a jaw end and each preferably being composed of an insulating material such as plastic to provide electrical shielding. The clasp lever is operatively associated with the base member for articulation on the base member at a point intermediate the ends of the lever. An electrically conductive closing spring is connected to the clasp base member. The spring has an intermediate upward projection, i.e., a deflection with spaced upright legs that extends up from the base to the lever and an upper closed end that functions somewhat in the nature of a fulcrum for the lever but, through its resiliency, also yieldably biases the jaw ends toward one another, i.e., to the closed position. The spring can be a leaf spring. One portion of the spring is a gripping portion positioned at the jaw end of the lever to serve as an electrically conductive jaw face. Preferably, an end portion of the closing spring adjacent the handle end of the base (the end opposite from the jaw) includes a terminal portion with a reverse bend having yieldable portions in opposition to one another on each side of this bend to serve as a receptacle for frictionally gripping a conductor, e.g., a pin connector which can be thrust through an opening and between the opposing yieldable portions of the spring.

27 Claims, 5 Drawing Sheets

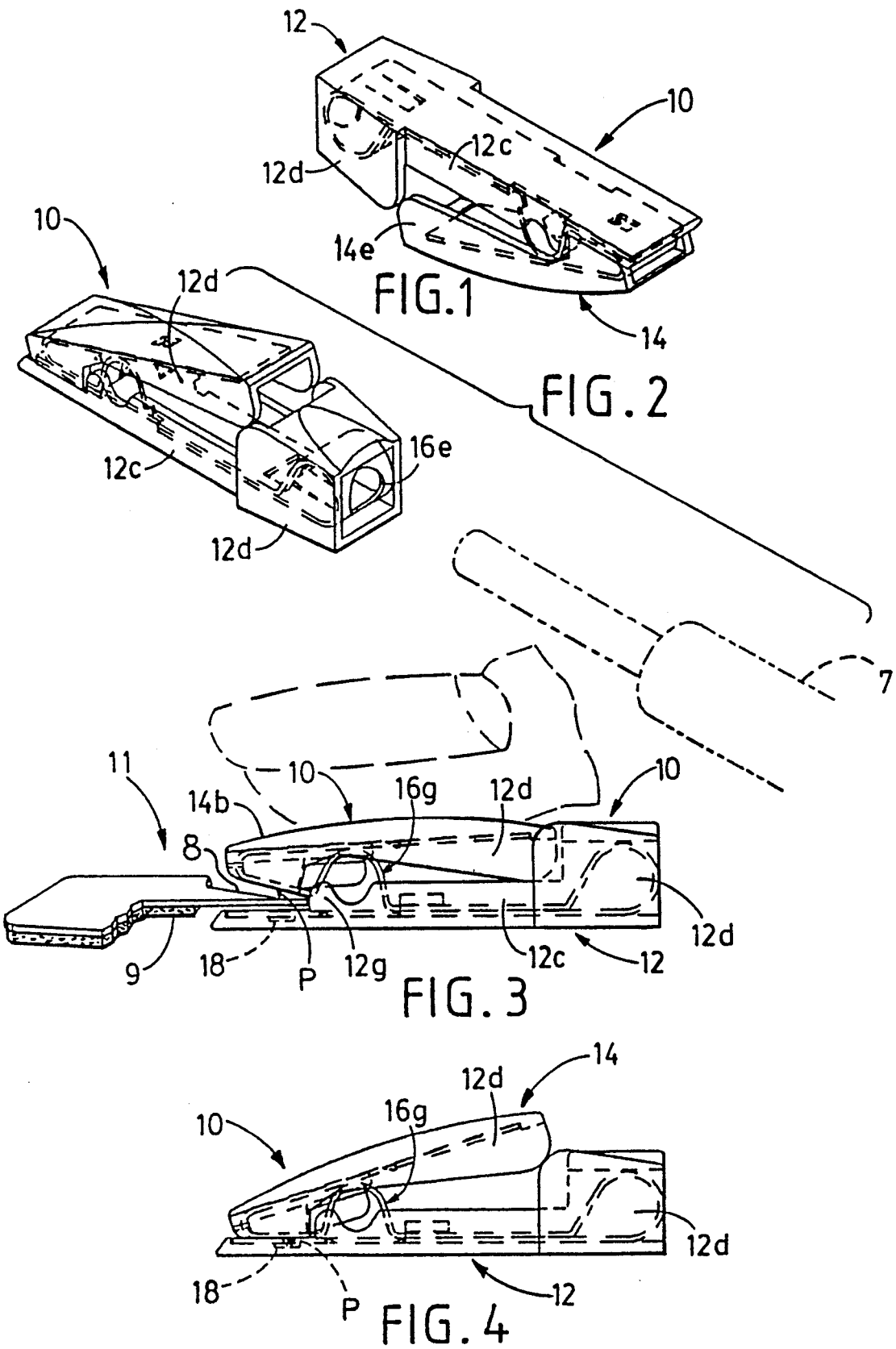

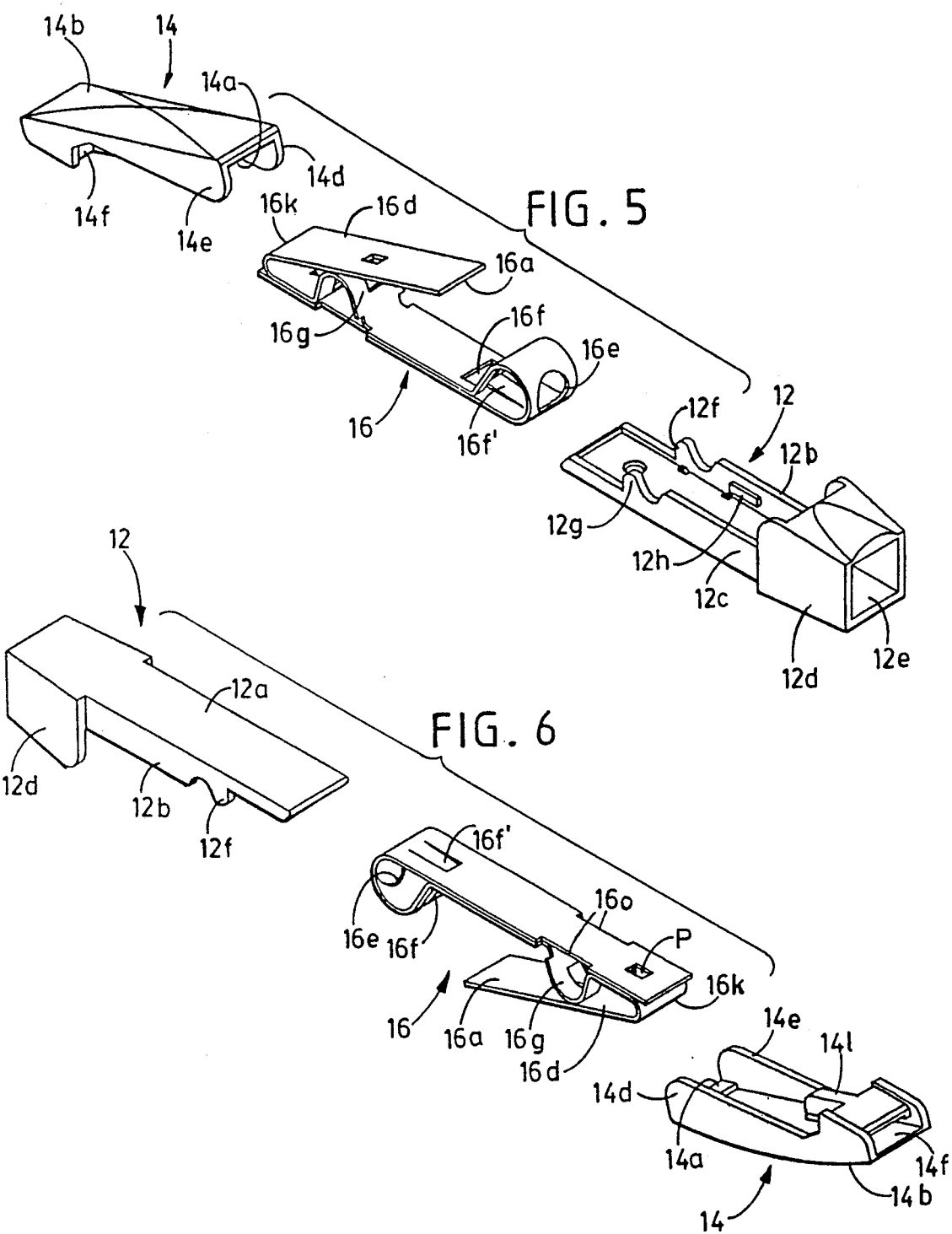

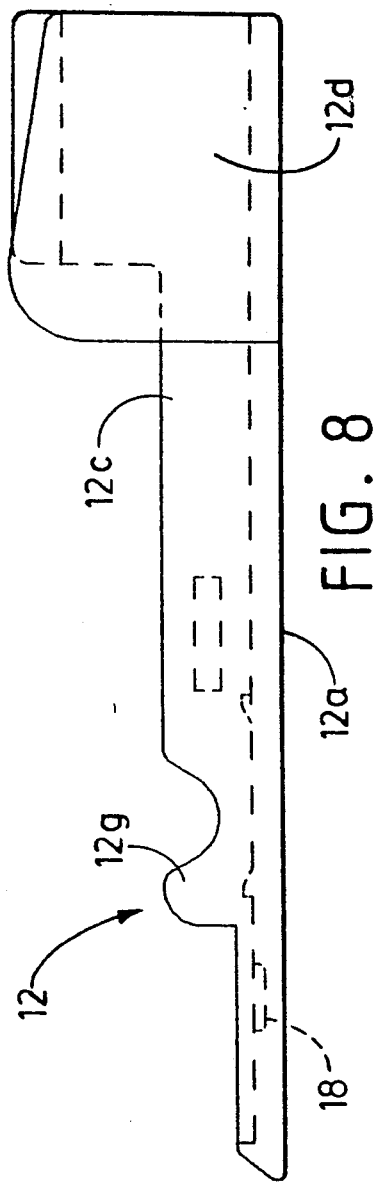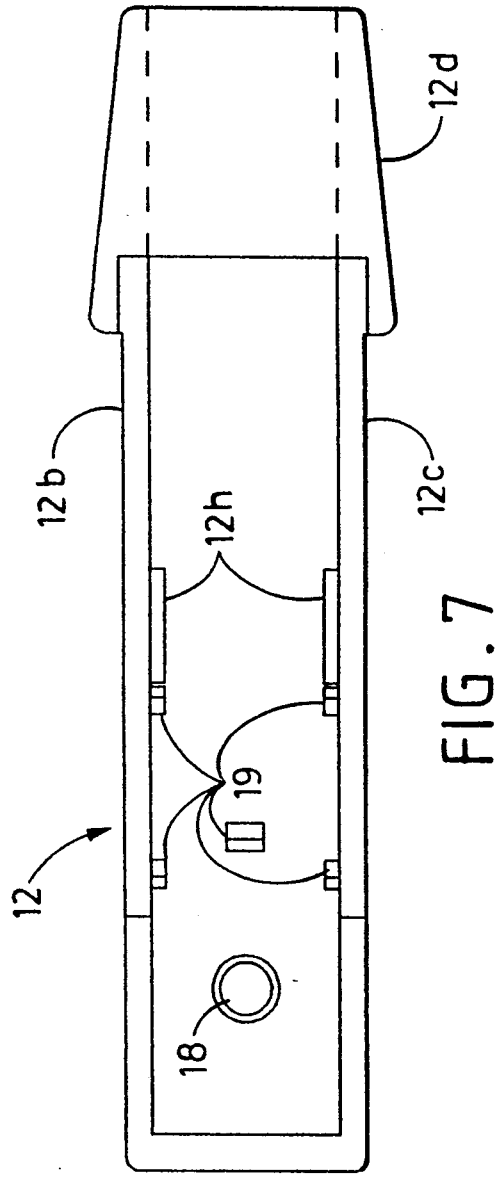
FIG. 8
FIG. 7

BIOMEDICAL ELECTRICAL CLASP

FIELD OF THE INVENTION

This invention relates to biomedical apparatus and more particularly to a spring-operated clasp for connecting conductors to biomedical electrodes that are placed in contact with the skin of a patient.

BACKGROUND OF THE INVENTION

A biomedical electrode is a flexible, electrically conductive sheet of material having a sticky surface which is placed in contact with the skin of a patient for transferring electromedical signals, such as cardiovascular signals, to electrocardiographic equipment or for stimulating the patient by applying electrical current through the electrode to the patient. Whether they are for stimulation or for electrocardiographic readings, i.e., monitoring, the flexible electrodes (referred to as external electrodes) are placed at selected locations on the skin of the patient and are held in place by adhesive. They include a conductive gel which provides the required electrical conductivity for transferring signals to or from the body through the electrode. These signals to or from the body through the electrode. These electrodes include a lateral extension (tab) on one side or a metal terminal, i.e., a steel snap member to which a wire can be connected.

The present invention is concerned with the provision of an improved connector or clasp for making electrical contact with such monitoring or stimulating electrodes by securely gripping the tab portion of the electrode or snap, as the case may be, as well as to provide an electrical connection with several sizes of male pin-type cable connectors that are now in common use for transferring electromedical signals.

Clasps previously available have been complicated in construction, subject to malfunction, and sometimes expensive to assemble. In addition, they did not always provide a strong gripping force or, in some cases, tended to be loose at the point of articulation so that the jaws of the clasp could wobble from side to side. Another problem was the requirement for using a threaded coupler or soldered connection between the electrical lead wire and the clasp. Another problem with many previously available clasps is that the gripping portion, i.e., the jaw, has only one conductive surface, causing an interruption in transfer of electrical signals when accidentally attached upside-down to the electrode tab which is only conductive on one side, usually its lower side.

A general objective of the invention is to provide an improved clasp that is especially well suited for use with diagnostic electrodes and is adapted to connect to both tab-type electrodes and to snap-type electrodes.

A further object is to provide a clasp that can be easily opened with moderate finger pressure but yet provides a strong, secure closing action for reliably gripping the electrode.

Another object is to provide a clasp that is more reliable in operation, less subject to damage or malfunction, and which can be easily and quickly assembled.

A further object is to employ a single spring that supports a gripping lever which closes the jaws and also provides a receptacle at the other end for pin-type connectors of various sizes that are now in commercial use. More specifically, it is an object to find a way of using a spring which is of a one-piece, i.e. unitary, construction that will eliminate the risk associated with a soldered joint formerly used, which is subject to breakage, so as to thereby guarantee an uninterrupted transfer of electrical signals from the gripping jaws to the receptacle end of the clasp to which is attached the pin connector at the end of a lead wire.

It is another object to provide a spring that is wider wire springs than presently used in the trade, so as to achieve a sturdier construction and larger contact surface area for maximum conductivity at the gripping end of the clasp.

Yet another object is to provide a simply constructed and reliable clasp having an articulated clasp lever (for opening and closing the jaws of the clasp) which is supported upon the base of the clasp by a one-piece spring that provides the spring action for closing the jaws of the clasp as well as for securing a pin connector to the clasp.

Another object is to find a way of preventing the clasp from accidentally contacting the sticky hydrogel portion of the flexible electrode which, when it occurs, will cause what is known as "base-line wander", a completely unacceptable condition that distorts the electrical signal received.

Another object is to provide a retaining hook or prong which will pierce the electrode tab yet cause less damage to the tab and, in addition, is inherently easier to remove from the tab when the jaws are open.

Yet another object is to find a way of preventing lead wires from becoming entangled between the gripping end portions of the clasp levers.

Still a further object is to provide resilient or yieldable gripping elements that slidably engage and yieldably contact opposing surfaces of a pin connector for securely gripping the pin to provide a reliable electrical connection therewith.

These and other more detailed and specific objects of the present invention will be apparent in view of the following description setting forth by way of example but a few of the various forms of the invention that will be apparent to those skilled in the art once the principles described herein are understood.

SUMMARY OF THE INVENTION

This invention provides a spring-operated biomedical electrical clasp which includes a clasp base means and a clasp lever, each having a handle end and a jaw end and each preferably being composed of an insulating material such as plastic to provide electrical shielding. The clasp lever is operatively associated with the base member for articulation on the base member at a point intermediate the ends of the lever. An electrically conductive closing spring is connected to the clasp base member. The spring has an intermediate upward projection, i.e., a deflection with spaced upright legs that extends up from the base to the lever and an upper closed end that functions somewhat in the nature of a fulcrum for the lever but, through its resiliency, also yieldably biases the jaw ends toward one another, i.e., to the closed position. The spring can be a leaf spring. One portion of the spring is a gripping portion positioned at the jaw end of the lever to serve as an electrically conductive jaw face. Preferably, an end portion of the closing spring adjacent the handle end of the base (the end opposite from the jaw) includes a terminal portion with a reverse bend having yieldable portions in opposition to one another on each side of this bend to serve as a receptacle for frictionally gripping a conductor, e.g., a pin connector which can be thrust through an opening and between the opposing yieldable portions of the spring.

THE FIGURES

FIG. 1 is a bottom perspective view of the clasp of the present invention;

FIG. 2 is a top perspective view of the clasp and in dotted lines a pin connector of the type commonly connected to a lead wire to which the clasp of the present invention is to be connected;

FIG. 3 is a side elevational view of the clasp with the jaws in the open position and a flexible electrode tab between the jaws;

FIG. 4 is a side elevational view of the clasp with the jaws in the closed position;

FIG. 5 is a top exploded perspective view of the clasp;

FIG. 6 is a bottom exploded perspective view of the clasp;

FIG. 7 is a plan view of the clasp base member on a larger than FIGS. 1-6;

FIG. 8 is a side elevational view of the clasp base of FIG. 7;

DETAILED DESCRIPTION OF THE INVENTION

Figure 11:
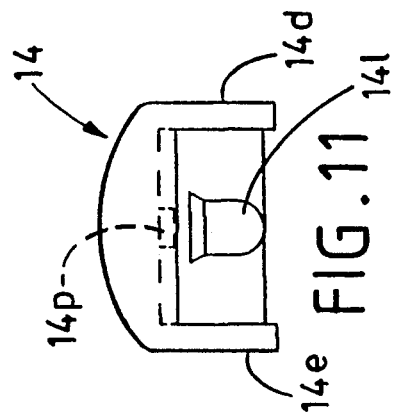
FIG. 11 is a right end elevational view of the lever.
Figure 9:
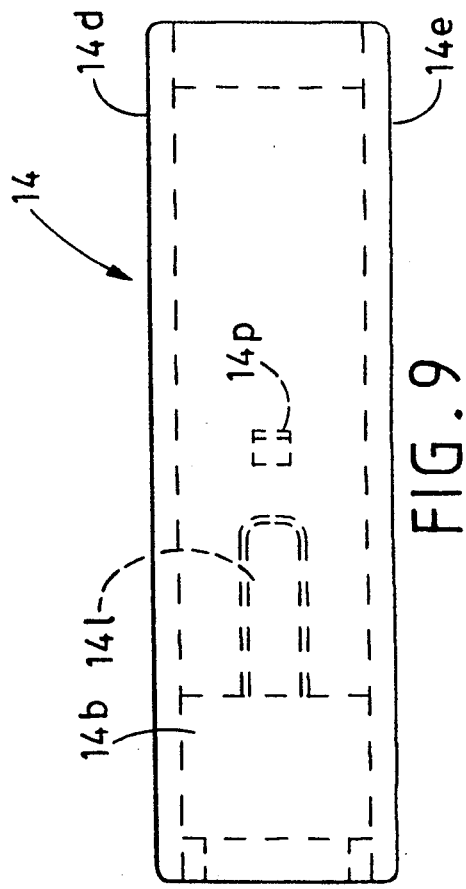
FIG. 9 is a top view of the clasp lever on a larger scale than illustrated in FIGS. 1-6.
Figure 10:
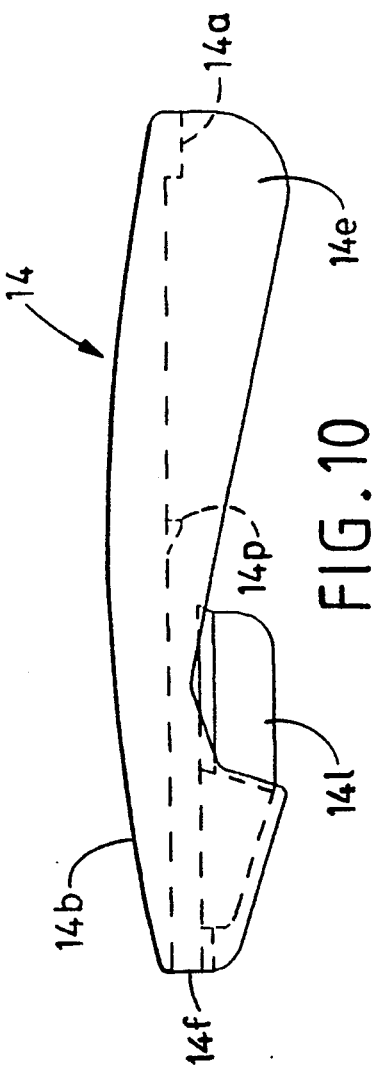
FIG. 10 is a side elevational view of the clasp lever of FIG. 9.

Refer now to FIGS. 1-4, which illustrate an electrical connector or clasp 10 in accordance with the present invention. The clasp 10 includes an elongated base member 12 (for convenience referred to as a "base") and clasp lever 14 which articulates with respect to the base 12 between an open position (FIG. 3) and a closed position (FIG. 4). The base 12 and lever 14 can be formed from any of a variety of materials such as metal or plastic, but are preferably formed from an electrically insulating or shielding material such as injection molded plastic, e.g., nylon which can be fiber reinforced as with glass fibers, if desired. As seen best in FIGS. 5 and 6, a spring 16 which closes the clasp 10 as will be more fully described below is a leaf type spring formed from a narrow strip of flat-rolled, annealed steel, e.g., ¼" wide and 0.015" to 0.018" inch thick. It can be plated, e.g., with coatings of copper and nickel to enhance conductivity.

The base 12 will now be described with reference to FIGS. 5-8. As seen in the figures, the base 12 is elongated, rectangular and has a flat center portion 12a. It includes a pair of longitudinally extending upright low side walls 12b and 12c which project from the flat center section 12a. The side walls 12b and 12c terminate at the left end of FIGS. 2-5 in a pair of upwardly extending fingers or stops 12f and 12g which, as shown in FIG. 3, limit the distance that tab 8 of skin-contacting electrode 11 can enter clasp 10. This prevents electrical contact with the gummy matrix 9 which, if it were to occur, would ruin the monitored electrical signals. The right end of the base 12 as seen in the figures includes a collar 12d surrounding a longitudinally extending central opening 12e. Projecting centrally from the side walls 12b and 12c are two opposed centrally extending retaining studs 12h. The retaining studs 12h help to hold the spring 16 in place during use. The studs 12h also provide firm pressure for keeping the jaw portions of the clasp 10 closed as will be described more fully below. At the jaw end of the base 12 is provided a round pocket 18 which accommodates a prong P which projects from an upper face of spring 16. Other retaining elements, such as studs 19, can be used to snap into openings 160 in spring 16 to help hold it in place.

Refer now to FIGS. 5, 6, 9 and 10 with reference to the construction of the clasp lever 14. As shown, the clasp lever 14 is elongated, flattened and generally rectangular as seen in plan view. It includes a handle end with an inner transverse rib 14a and a jaw end 14b. The lever 14 has a pair of low, downwardly extending side walls 14d and 14e and a tubular collar 14f (FIGS. 5, 6 and 10) through which a portion 16d of spring 16 extends after assembly. The collar 14f has a central flange 141 which, during assembly, snaps into a like-shaped opening (FIGS. 5 and 6) in the deflection 16g of spring 16. A lug 14p also snaps into an opening in spring 16 to hold it in place.

During assembly, the upper free end of the spring 16 at 16a in FIG. 5 is thrust through the collar 14f to securely hold the lever 14 in place on spring 16. It will be seen that in the resting position of FIG. 4, the closing spring 16 will draw the jaw end 14b of the lever 14 to a position proximate to the jaw end of the base 12, and the handle end 14b of the lever 14 will be elevated where it can be easily pressed down with a thumb or finger to open the jaws as shown in FIG. 3.

The closing spring 16 will now be described in more detail with reference to FIGS. 5, 6 and 11. As shown in the figures, the closing spring 16 is a leaf type spring that has three main sections, including two adjacent sections $16c'$ and $16c^2$ which are joined by a reverse bend 16b at the right end of the clasp 10 as seen in the figures, and an upper inclined section 16d terminating in the free end 16a. The bend 16b preferably is a circular arc with a central opening 16e to receive a pin connector 7 (FIG. 2). The reverse bend 16b in this way serves as a pin receptacle for an electrode pin 7 (FIG. 2). On opposite sides of the bend 16b are opposing resilient and yieldable tongue-shaped contact members 16f, 16f' enable the receptacle to frictionally grip the pin connector 7 when inserted through the opening 16e.

During assembly, the reverse bend 16b is inserted into the opening 12e of the collar 12d of the base 12. The yieldable portions 16f and 16f' provide a smooth sliding contact with the electrical terminal pin 7 (FIG. 2) when it is slid into the opening 16e to provide electrical contact therewith. The lower contact members 16f' can have a trough-shaped cross-section to conform to the pin 7 for guiding the pin and for making electrical contact with the pin as it passes through the opening 16e into the clasp 10. The opposing contact members 16f and 16f' press down on the pin 7 due to their own resiliency and the resiliency of the reverse bend 16b of the spring 16 to hold the pin 7 securely in place and establish good electrical contact.

Figure 12:
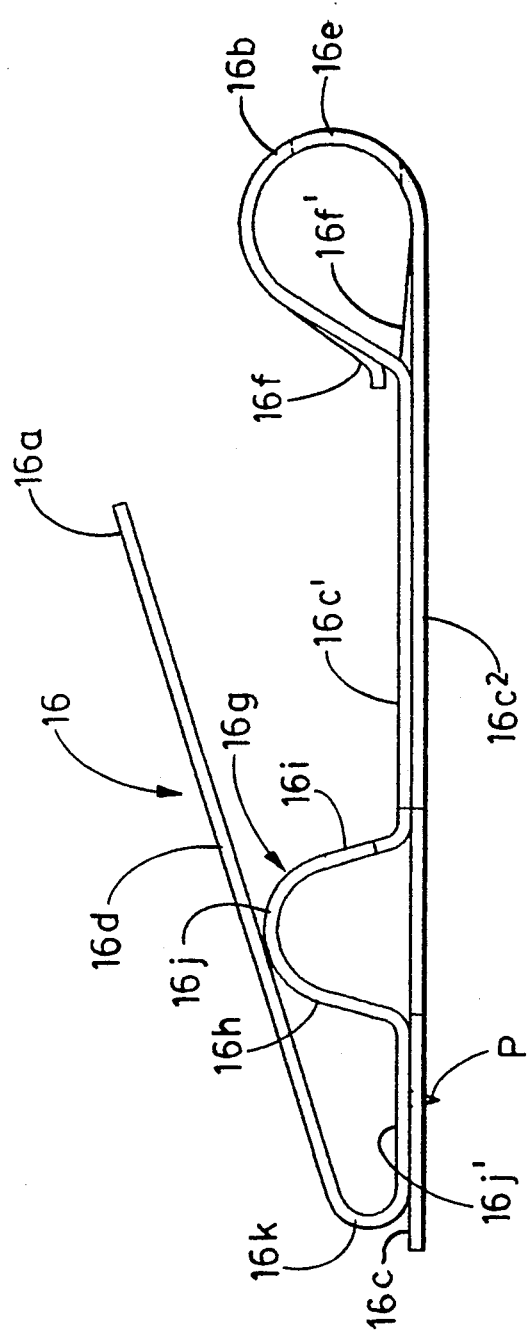
FIG. 12 is a side view on a larger scale of the closing spring.

The base portion at $16c^2$ has a free end at the left end of the clasp 10 which serves as an electrical contact surface for the lower jaw. The intermediate section $16c'$ of the spring 16 is provided with an upwardly projecting deflection 16g having longitudinally spaced upright legs 16h and 16i that extend from the base 12 toward the lever 14. As shown in FIG. 12, the upper end of legs 16h and 16i join one another at an arch-shaped free upper end portion designated 16j. The arch-shaped free upper end portion 16j of the deflection 16g which is located adjacent to the lever 14 (FIG. 4) functions somewhat in the nature of a fulcrum for the lever 14. However, through its resiliency it also biases the jaws toward one another, i.e., to the closed position. As seen in FIG. 12, a horizontal portion 16j' of spring 16 extends from the deflection 16g to the jaw end 14b of lever 14. The spring 16 has a bend 16k therein adjacent to the jaw end 14b of lever 14 and the spring has a lever supporting portion 16d extending from the bend 16k longitudinally of lever 14 that is inclined at an oblique angle with respect to the base 12. The lever supporting portion 16d is connected to the lever 14 for supporting it. It will be seen in FIG. 12 that before finger pressure is applied, i.e., when the spring 16 is in a relaxed condition, to horizontal portion 16j' to the left of the deflection 16g contacts the left end of the bottom portion 16c². In this way, portion 16j' and the adjacent end of portion 16c form jaw faces which securely grip the tab 8 of the skin-contacting electrode 11 (FIG. 3) to provide a reliable electrical and mechanical connection with the electrode 11. The contact surfaces of the jaw faces can be serrated, if desired, to provide more surface friction and to provide a more secure grip on the tab 8 of the electrode 11. In this case, at the center of portion 16j' is a pointed prong P or hook which is bent downwardly to project through a central opening in the jaw face near the left end of portion 16c to pierce and hold the tab 8 securely but yet release it reliably when the jaws are opened because the tab 8 tends to fall away from the prong P. In addition, the prong P, because it is on top, has little tendency to damage the metal coating on the bottom of tab 8.

Assembly of the clasp 10 is easily accomplished by sliding the pin receptacle portion within the reverse bend 16b of the spring 16 into the collar 12d. As this is done, both sections 16c' and 16c² slide under the opposed retaining studs 12h. The lever 14 is then slid into place on the upper jaw portion 16a of the spring 16 and forced toward the right as seen in FIGS. 2–4 until the bend 16k slides through the slot 14f in the lever 14. The upper portion 16a of the spring 16 will also come to rest between the side walls 14d and 14e, with its free end adjacent the inner surface of the transverse rib 14a. The clasp 10 is then ready for use. Since all electrical connections are made through adjacent metal jaw surfaces of spring 16 and via the receptacle within the reverse bend 16b at the opposite end of the spring 16, a reliable electrical connection is achieved through a single working part, namely, the spring 16. This makes the clasp 10 more reliable because it eliminates the possibility of an open circuit.

It will be noticed that the deflection 16g acts somewhat as a fulcrum by permitting articulation of the lever 14. It also supports the lever 14. The deflection 16g thus functions to replace hinges formerly used in biomedical electrical clasps. Since a true hinge is not needed, the closing action is smooth and there is little opportunity for parts to wobble. In addition, electrical continuity is assured and assembly is simplified, thereby reducing production costs.

One preferred method of forming the spring 16 will now be described. The spring 16 is about 0.25 inch wide and about 4.4 inches long. It can be formed from a strip of 1095 annealed steel (flat on roll) and is then bent to the shape shown. Low carbon, flat-rolled steel having a nominal thickness of about 0.015 inch to 0.018 inch can be employed. The springs are then heat-treated at a temperature that will produce a Rockwell hardness level of from 47 to 52. The spring is next deburred, preferably by tumbling the spring in a vat filled with an abrasive liquid for a period of about 30 minutes to 45 minutes. Approximately 2,500 springs are put in a drum at one time. This smooths out the rough places in the spring steel and allows for better plating. A copper flash is then plated on all surfaces to a thickness of 0.00005 inch. Next, an electroless nickel plating is applied to a thickness of 0.0001–0.0002 inch. The parts are then baked within one hour of plating for eight hours at 350° F. to 375° F. The lever 14 can have a length of about 1.15 inches and a width of about 0.32 inch. The base 12 can have a length of about 1.56 inches and a width of about 0.32 to about 0.41 inch, with other parts of proportionate size.

The present invention provides a clasp structure having a receptacle with the reverse bend 16b adapted to accommodate a variety of different pin sizes. For example, manufacturers commonly employ terminal pins having diameters of, say, 2 mm, 3 mm and 4 mm. All of these sizes can be accommodated by the receptacle of the present invention. The clasp 10 does not require a soldered connection between the pin 7 and clasp 10, nor a threaded connection which adds cost and takes time to assemble. Consequently, the receptacle can be considered universal with respect to its ability to accommodate pin terminals of various sizes.

It can also be seen that the base 12 and the lever 14 provide electrical insulation and shielding. In this way, they reduce the opportunity for the clasp 10 make electrical contact with any other conductors that may be in the vicinity of the patient to prevent extraneous signals from entering the system or from interferring with the signals being transferred. In addition, they help prevent electrical shocks in the event the electrode is used for heart stimulation, and the stops 12f and 12g prevent accidental electrical contact between the jaws and the gummy matrix 9 of skin electrode 11. As can be seen in FIG. 4, the side walls 14d and 14e prevent lead wires from becoming caught and entangled between the base 12 and the lever 14.

Another important advantage of the invention is that the deflection 16g provides an opening for the metal snap of a snap-style electrode. Consequently, the invention can be used with all skin electrodes, whether they are the tab-type electrode as shown in FIG. 3 or the snap-type electrode which has a metal snap member that extends from the upper surface of the electrode. To make contact with a snap, the clasp 10 is turned on its side and the snap (not shown) is introduced into the deflection 16g from the side of the clasp 10, i.e., between the legs 16i and 16h. The jaws are then allowed to close upon the head of the snap element. When the clasp 10 is closed, portions of the base 12 just beneath the deflection 16g force the steel snap element into electrical contact with the underside of deflection 16g to hold the snap in place.

A surprising benefit of the invention is that, in spite of the firm closing pressure of the jaws made possible by the downward force of the retaining studs 12h on spring 16, the jaws are nevertheless quite easy to open because of the fulcrum effect provided by the deflection 16g. This allows the jaws to be opened easily by applying pressure with the index finger and thumb, yet the jaws hold the tab 8 with a firm grip.

Many variations of the present invention within the scope of the appended claims will be apparent to those skilled in the art once the principles described herein are understood.

What is claimed is:

1. A spring-operated biomedical electrical clasp for gripping a biomedical skin-contacting electrode which is applied to the skin of a patient, said clasp comprising:
   a clasp base and a separate clasp lever each having a handle end and a jaw end,
   said clasp lever being operatively associated with the clasp base for articulation relative to the clasp base intermediate the ends of the lever,
   an electrically conductive spring member having a portion connected to the clasp base,
   said spring member having a portion connected to the clasp lever,
   said spring member yieldably biasing the jaw end of the lever toward a closed position with respect to the jaw end of the base,
   said spring member having a jaw face portion adjacent the jaw end of said lever and said base to define an electrically conductive jaw surface that is a portion of said spring, said spring biasing the jaw surface toward an opposing jaw surface for releasably gripping said biomedical electrode and for making electrical contact therewith, and
   the spring has a reverse bend at the handle end of the base, said reverse bend includes an opening to provide an electrical coupling receptacle for receiving and frictionally securing an electrically conductive pin member to transfer electrical signals to or from the clasp.

2. The clasp of claim 1 wherein the reverse bend has a yieldable tongue yieldably biased to press against the pin member when the pin member is inserted in the opening.

3. The clasp of claim 2 wherein the spring has a pair of said yieldable tongues opposing one another adjacent the reverse bend to frictionally hold the pin member and to establish electrical contact therewith.

4. The clasp of claim 3 wherein one of the tongues has a trough-shaped cross-section positioned in alignment with the axis of the pin member when inserted into the clasp for making electrical contact therewith.

5. A spring-operated biomedical electrical clasp for gripping a biomedical skin-contacting electrode to be applied to the skin of a patient, said clasp comprising:
   a clasp base and a clasp lever each having a handle end and a jaw end,
   said clasp lever being operatively connected by means of a leaf spring to the clasp base for articulation relative to the clasp base,
   said leaf spring is connected between the lever and the base for supporting the lever on the base and for closing the clasp by yieldably biasing the jaw ends of the base and lever toward one another,
   the leaf spring has a lower portion positioned proximate to the clasp base and connected thereto,
   said leaf spring has an intermediate section with a deflection therein extending upwardly from the clasp base toward the lever, and
   the spring has a lever supporting portion connected to the lever and located on the opposite side of the deflection from said lower portion,
   and the deflection has an upper portion positioned adjacent to the lever that acts as a fulcrum for the lever when manual pressure is applied to the lever for opening the clasp.

6. The clasp of claim 5 wherein the deflection has a pair of spaced apart legs with an opening therebetween that can be used to receive a metal snap element of a snap-style electrode.

7. The clasp of claim 5 wherein the base and lever are composed of an insulating material to provide an electrical shield for the clasp.

8. The clasp of claim 5 wherein the leaf spring includes a bend adjacent the jaw end of the base, the intermediate section of said spring extends from said bend toward the handle end of the base and said spring has a reverse bend proximate the handle end of the base with contact members on opposite sides of the bend and a pin opening in the bend to receive a terminal pin to thereby serve as a pin receptable for frictionally engaging said terminal pin.

9. The clasp of claim 5 wherein the leaf spring includes a pair of opposing electrically conductive faces to receive a portion of said skin-contacting electrode therebetween at the jaw end of the lever and base, and said electrode is engaged by the opposing faces of the same leaf spring to establish electrical contact with the clasp.

10. The clasp of claim 5 wherein the spring has a receptacle portion at the handle end of the base and the receptacle portion of the spring includes an opening for receiving and contact means as a part of the spring to frictionally secure an electrically conductive pin member within the receptacle for transferring electrical signals to or from the pin member to the clasp.

11. A spring-operated biomedical electrical clasp for a biomedical electrode comprising:
   first and second articulated clasp members, the clasp members each having a jaw end and a handle end,
   said clasp members being connected together by means of a leaf closing spring, said spring yieldably biasing the jaw ends of the clasp members toward one another, said second clasp member comprises a base,
   said leaf closing spring having end portions extending lengthwise of each of the clasp members,
   said spring also having an intermediate section with a bend adjacent the jaw end of the clasp members,
   a deflection in the intermediate section of the spring, said deflection extending between the two clasp members and having a portion raised above the base and positioned adjacent to the first clasp member to act as a fulcrum for the first clasp member and to help support the first clasp member as well as biasing the jaw end of the first clasp member toward the jaw end of the base.

12. The clasp of claim 11 wherein the closing spring has a portion that includes an electrical coupling receptacle with a contact member as a part of the spring for receiving and securing an electrically conductive pin member to the clasp.

13. The clasp of claim 12 wherein the receptacle has an opening to receive the pin member and the receptacle has a tongue which yieldably presses against the pin member when the pin member is inserted into the opening in the clasp.

14. The clasp of claim 12 wherein the spring has an arcuate bend therein and the contact member is a yieldable portion adjacent the arcuate bend for frictionally holding the pin member in place and to establish a good electrical connection with the pin.

15. The clasp of claim 11 wherein two opposing portions of the spring define electrically conductive jaw faces at the jaw end of the clasp members to establish an electrical circuit through the spring with said electrode.

16. The clasp of claim 12 wherein a portion of the spring adjacent the receptacle has a trough-shaped cross-section for guiding the pin member when said pin member is inserted into the clasp.

17. The clasp of claim 11 wherein said leaf closing spring has lower and upper adjacent opposing electrically conductive cooperating jaw face portions located respectively at the jaw end of the lower portion of the spring and a jaw end of the intermediate section of the spring for gripping and establishing electrical contact with the biomedical electrode.

18. The clasp of claim 17 wherein one of the jaw faces has a prong extending therefrom for piercing said electrode.

19. The clasp of claim 11 wherein the spring is coated with an electrically conductive substance and the lever and base are formed from an electrically insulating plastic resin.

20. The spring-operated biomedical electrical clasp of claim 11 wherein one of the clasp members includes a stop member between the jaw ends of the clasp members and the deflection in the spring for limiting a distance that the biomedical electrode can enter the clasp to prevent undesirable electrical contact with a matrix portion of said biomedical electrode.

21. The spring-operated biomedical electrical clasp of claim 11 wherein the deflection is an archshaped portion of said spring having a pair of upright legs extending from the base toward the lever and the legs are joined together at their upper ends to define the arch-shaped portion whereby a snap member provided on said biomedical electrode can be introduced into the deflection between said legs from one side of the clasp and the jaws then allowed to close upon a head of said snap member.

22. A biomedical clasp for making contact with a biomedical electrode, said clasp comprising,
a clasp base and a clasp lever, each including cooperating opposing jaws at one end for gripping the biomedical electrode therebetween,
a leaf spring connected between the clasp base and the clasp lever for closing the jaws,
said spring having a flat section,
retaining means for securing the flat section of the spring in a fixed position relative to the clasp base for forcing the jaws together,
a deflection located between the opposing jaws and the retaining means and said deflection is positioned to extend between the base and the lever, said deflection having a free upper end adjacent the lever to serve as a fulcrum for the lever,
said fulcrum allowing the jaws to be opened easily when finger pressure is applied to the lever and engagement between the retaining means and the spring providing a firm closing pressure between the jaws of the clasp.

23. The clasp of claim 22 wherein the deflection is an arch-shaped portion of said spring having a pair of upright legs extending from the base toward the lever and being joined at their upper ends in an arch, and said arch being adapted to support a lower surface of said lever to serve as said fulcrum for said lever when finger pressure is applied to a free end of said lever opposite the jaw end thereof.

24. The clasp of claim 23 wherein a portion of the spring extends from said deflection to a jaw end of said lever, said spring has a bend therein adjacent the jaw end of said lever and said spring has a lever supporting portion extending from said bend longitudinally of said lever and when the clasp is closed said lever supporting portion of said spring is inclined at an oblique angle with respect to said base and is connected to said lever to support said lever.

25. A spring-operated biomedical electrical clasp for gripping a biomedical skin contacting electrode that is applied to the skin of a patient, said clasp comprising:
an elongated clasp base having a handle end and a jaw end portion,
a clasp lever connected to the clasp base and said clasp lever also having a handle end and a jaw end portion,
said clasp lever being operatively associated with the clasp base for movement about a point of articulation relative to the clasp base to permit the jaw end portions of the clasp base and clasp lever to open and close for gripping the skin contacting electrode,
a closing spring operatively associated between the clasp base and the clasp lever for yieldably biasing the jaw end portions toward a closed position for causing the jaw end portions to grip the electrode,
an electrically conductive jaw face member connected to at least one of said jaw end portions to define an electrically conductive jaw surface positioned between the jaw end portions of the clasp base and clasp lever,
electrically conductive means connected to the jaw face for establishing electrical contact between the jaw face and a lead wire that is to be electrically coupled to the clasp, and
at least one stop means as a part of the clasp between the jaw end portions of the clasp base and clasp lever adjacent to the electrically conductive jaw face for engaging and limiting a distance that the biomedical skin contacting electrode can enter the clasp to prevent undesired electrical contact between a matrix portion of the biomedical electrode and the electrically conductive jaw face,
said stop means is positioned upon one of said jaw end portions between the electrically conductive jaw face and the point of articulation of said clasp,
whereby the prevention of electrical contact between said matrix and the clasp avoids impairment of electrical signals that would otherwise result from such contact.

26. The spring-operated biomedical electrical clasp of claim 25 wherein the clasp includes a pair of laterally spaced apart stop members positioned upon one of said jaw end portions adjacent to the electrically conductive jaw surface and positioned between the electrically conductive jaw face and said point of articulation and said stop members extend from one of said jaw end portions toward the other of said jaw end portions.

27. The clasp of claim 26 wherein the stop members are a part of said clasp base and extend upwardly therefrom toward the clasp lever.

* * * * *